US005756838A

United States Patent [19]

Davis et al.

[11] Patent Number: 5,756,838
[45] Date of Patent: May 26, 1998

[54] METHOD OF ASYMMETRICALLY SYNTHESIZING OPTICALLY ACTIVE COMPOUNDS USING SUPPORTED PHASE CHIRAL SULFONATED BINAP CATALYST

[75] Inventors: Mark E. Davis; Kam To Wan, both of Pasadena, Calif.

[73] Assignee: California Institute of Technology, Pasadena, Calif.

[21] Appl. No.: 515,644

[22] Filed: Aug. 16, 1995

Related U.S. Application Data

[62] Division of Ser. No. 199,086, Feb. 22, 1994, abandoned.

[51] Int. Cl.$^6$ .................. C07C 59/00; C07C 59/11; C07C 69/02

[52] U.S. Cl. .................. 562/553; 562/433; 560/15; 560/19; 556/479; 568/451; 549/523

[58] Field of Search .................. 562/553, 433; 560/15, 19; 556/479; 549/523; 568/451

[56] References Cited

U.S. PATENT DOCUMENTS

| | | | |
|---|---|---|---|
| 4,399,312 | 8/1983 | Russell et al. | 568/454 |
| 4,605,750 | 8/1986 | Kumobayashi et al. | 556/22 |
| 4,654,176 | 3/1987 | Dang et al. | 260/505 |
| 4,691,037 | 9/1987 | Yoshikawa et al. | 556/18 |
| 4,766,227 | 8/1988 | Sayo et al. | 556/21 |
| 4,947,003 | 8/1990 | Davis et al. | 568/454 |
| 4,954,644 | 9/1990 | Sayo et al. | 556/14 |
| 4,994,427 | 2/1991 | Davis et al. | 502/166 |
| 4,994,590 | 2/1991 | Takaya et al. | 556/21 |
| 5,012,002 | 4/1991 | Kumobayashi et al. | 568/17 |
| 5,159,093 | 10/1992 | Taketomi et al. | 556/136 |
| 5,177,231 | 1/1993 | Manimaran et al. | 562/496 |
| 5,187,135 | 2/1993 | Kolich et al. | 562/496 |
| 5,187,136 | 2/1993 | Klobucar et al. | 556/45 |
| 5,187,281 | 2/1993 | Kolich et al. | 562/496 |
| 5,190,905 | 3/1993 | Kolich et al. | 562/496 |
| 5,202,472 | 4/1993 | Manimaran et al. | 562/493 |
| 5,202,473 | 4/1993 | Chan et al. | 562/496 |
| 5,202,474 | 4/1993 | Chan | 562/496 |
| 5,210,243 | 5/1993 | Kolich | 556/18 |
| 5,274,146 | 12/1993 | Ishizaki et al. | 556/14 |
| 5,274,183 | 12/1993 | Herrman et al. | 562/35 |
| 5,324,861 | 6/1994 | Ishizaki et al. | 568/454 |
| 5,347,045 | 9/1994 | Herrmann et al. | 562/35 |
| 5,510,503 | 4/1996 | Laue et al. | 556/21 |
| 5,563,295 | 10/1996 | Takaya et al. | 562/496 |
| 5,565,398 | 10/1996 | Herrmann et al. | 556/21 |

FOREIGN PATENT DOCUMENTS

| | | | |
|---|---|---|---|
| 0 133 127 | 7/1983 | European Pat. Off. | C07F 9/50 |
| 2 489 308 | 9/1981 | France | C07C 47/02 |
| 55-61937 | 5/1980 | Japan | 502/155 |

OTHER PUBLICATIONS

Kam–to Wan & Mark E. Davis, "Ruthenium (II)–Sulfonated BINAP: A Novel Water–Soluble Asymmetric Hydrogenation Catalyst", Tetrahedron: Asymmetry vol. 4, No. 12, 1993, pp. 2461–2467.

Kam–to Wan & Mark E. Davis, "Asymmetric Hydrogenation in Water by a Rhodium Complex of Sulfonated 2,2–Bis (diphenylphosphine)–1, 1'–binaphthyl (binap)", J. Chem. Soc. Chem. Commun., 1993, pp. 1262–1264.

R. Noyori, et al., "BINAP: An Efficient Chiral Element for Asymmetric Catalysis," Acc. Chem. Res. 1990, 23, 345–350.

R. Noyori, "Centenary Lecture: Chemical Multiplication of Chirality: Science and Applications," Chem. Soc. Rev. 1989, 18, 187–208.

A. Miyashita, et al., "Synthesis of 2,2'-Bis(diphenylphosphino)-1,1'-binaphthyl (BINAP), an Atropisomeric Chiral Bis(triaryl)phosphine, and Its Use in the Rhodium(I)–Catalyzed Asymmetric Hydrogenation of α–(Acylamino)acrylic Acids," J. Am. Chem. Soc. 1980, 102, 7932–7934./

A. Miyashita, et al., "2, 2'–Bis (diphenylphosphino)–1,1'–binaphthyl (BINAP): A New Atropisomeric Bis(triaryl)phosphine. Synthesis and Its Use in the Rh(I)–Catalyzed Asymmetric Hydrogenation of α–(Acylamino) acrylic Acids," Tetrahedron vol. 40, No. 8, pp. 1245–1253 (1984).

T. Ohta, et al., "BINAP–Ruthenium (II) Dicarboxylate Complexes: New, Highly Efficient Catalysts for Asymmetric Hydrogenations," Inorg. Chem. 1988, 27, 566–569.

R. Noyori, et al., "Enantioselective Catalysis with Metal Complexes. An Overview," R. Scheffold (Ed.) Modern Synthetic Methods 1989, vol. 5, pp. 115–198.

*Primary Examiner*—Nicky Chan
*Attorney, Agent, or Firm*—Limbach & Limbach

[57] ABSTRACT

The present invention relates to water soluble chiral sulfonated 2,2'-bis(diphenylphosphino)-1,1'-binaphthyl and its use as organometallic catalysts for asymmetric synthesis of optically active compounds. Asymmetric reactions of the present invention include those reactions in which organometallic catalysts are commonly used. Such reactions include, but are not limited to, reduction and isomerization reactions on unsaturated substrates and carbon—carbon bond forming reactions. Examples of such reactions include, but are not limited to, hydrogenation, hydroboration, hydrosilylation, hydride reduction, hydroformylation, alkylation, allylic alkylation, arylation, alkenylation, epoxidation, hydrocyanation, disilylation, cyclization and isomerization reactions.

The catalysts of the present invention provide the advantage of functioning in the presence of water without loss in enantioselectivity relative to the nonsulfonated BINAP catalyst in an organic solvent. As a result, the catalysts of the present invention may be employed in water, water miscible solvents, in aqueous-organic two phase solvent systems and in supported aqueous phase catalysts in organic solvents without loss in enantioselectivity. Further, the catalysts of the present invention may also be effectively employed in highly polar solvents such as primary alcohols and ethylene glycol.

The present invention also relates to a method for conducting asymmetric reactions on prochiral unsaturated bonds contained within a compound using the water soluble chiral sulfonated 2,2'-bis(diphenylphosphino)-1,1'-binaphthyl organometallic catalysts of the present invention.

17 Claims, 3 Drawing Sheets

Supported Aqueous Phase Catalysis

METHOD OF ASYMMETRICALLY SYNTHESIZING OPTICALLY ACTIVE COMPOUNDS USING SUPPORTED PHASE CHIRAL SULFONATED BINAP CATALYST

This is a divisional of application Ser. No. 08/199,086, filed Feb. 22, 1994, now abandoned.

The U.S. Government has certain rights in this invention pursuant to Grant No. CTS-9021017 awarded by the National Science Foundation.

TECHNICAL FIELD

The present invention is generally directed to water-soluble sulfonated chiral diphenyl phosphine catalysts useful for the asymmetric synthesis of optically active compounds. More specifically, the present invention relates to chiral sulfonated BINAP catalysts.

BACKGROUND OF THE INVENTION

The development of effective asymmetric reactions that enable the enantioselective formation of one chiral center over another continues to be an important area of research. One such asymmetric reaction involves the introduction of a chiral center into a molecule through the enantioselective hydrogenation of a prochiral olefin using a transition metal catalyst bearing chiral organic ligands. Numerous chiral phosphine catalysts have been developed to enantioselectivity introduce chiral centers to prochiral olefins, carbonyls and imines with high enantiomeric excess. One such class of chiral catalysts employs the chiral phosphine ligand 2,2'-Bis (diphenylphosphino)-1,1'-binaphthyl (hereinafter referred to as "BINAP". References reporting enantioselective reactions using the BINAP ligand include: Wu, et al., *Tetrahedron Letters* (1993) 34:(37) 5927–5930; Wu, et al., *Tetrahedron Letters* (1992) 33:6331–6334; Tani, et al., *J. Chem. Soc. Chem. Commun.* (1982) 600; Tani, et al., *Angew Chem. Int. Ed. Engl.* (1985) 24(3):217–219; Naruta, et al., *Tetrahedron Letters* (1987) 28:4553–4556; Hodgson, et al., *J. Organomet. Chem.* (1987) 325:627630; Hayashi, et al., *J. Am. Chem. Soc.* (1988) 110:5579–5581; Hayashi, et al., *J. Am. Chem. Soc.* (1989) 111:3426–3428; Kollar, et al., *J. Molecular Catalysis* (1991) 67:191–198; Collman, et al., *J. Chem. Soc. Chem. Commun.* (1993) 428; Murakami, et al., *Bull. Chem. Soc. Jpn.* (1992) 65:3094–3102; Yamaguchi, et al., *Tetrahedron Asymmetry* (1991) 2(7): 663–666; Burgess, et al., *Tetrahedron Asymmetry* (1991) 2(7): 613–621; Ozawa, et al., *Tetrahedron Letters* (1993) 34(15):2505–2508; Ozawa, et al., *Tetrahedron Letters* (1992) 33(11):1485–1488; Ozawa, et al., *Chemistry Letters* (1992) 2177–2180; Kagechika, et al., *J. Org. Chem.* (1991) 56:4093–4094; Sakamoto, et al., *Tetrahedron Letters* (1992) 33:68456848; Brunner, et al., *J. Organometallic Chem.* (1993) 456:71–75; Trost, et al., *J. Amer. Chem. Soc.*, (1980) 102:7932–7934; Miyashita, et al., *Tetrahedron* (1984) 40(8):1245–1253; Waldman, et al., "Selectivity in Catalysis," M. E. Davis and S. L. Snib, Eds. ACS Symposium Series 517 (1993); Ozawa, et al., "Selectivity in Catalysis," M. E. Davis and S. L. Snib, Eds. ACS Symposium Series 517 (1993); Chan, et al., "Selectivity in Catalysis," M. E. Davis and S. L. Snib, Eds. ACS Symposium Series 517 (1993); Dunina, et al., "Homogeneous Catalysis By The Optically Active Complexes Of Transition Metals And Its Application In The Synthesis Of Bioactive Molecules" *J. Org. Chem. USSR* (1993) 28:1547–1600, 1913–1971; WO 90/15790; WO 92/09552.

second important area of research relates to the development of water-soluble organometallic catalysts. Conventionally, catalytically active organometallic complexes have been applied as homogeneous catalysts in solution in the organic reaction phase. Difficulties associated with recovery of the homogeneous catalysts from the reactants and products diminish the utility of these homogeneous catalysts, especially when the cost of the catalyst is high or where there is the need to isolate the reaction products in high purity.

One mode in which water soluble organometallic catalysts have been used is in two phase systems comprising an aqueous phase and a water immiscible phase (e.g. ethyl acetate-water). Separation of the organometallic catalyst from organic reactants and products is greatly simplified due to the insolubility of the catalyst in the water immiscible phase. However, in some instances, the utility of the two phase system has been limited by a lack of substrate and/or reactant solubility in the aqueous phase and by the limited interfacial area between the two phases. For example, in the case of hydrogenation reactions, the solubility of dihydrogen in water at 25° C. and 1 atm is $8.53 \times 10^{-4}$ M, over four times smaller than the solubility of dihydrogen in ethanol ($38.2 \times 10^{-4}$ M).

Supported aqueous phase organometallic catalysts (SAP) have been developed to overcome some of the shortcomings associated with two phase reaction systems. In particular, SAP catalysts greatly enhance the interfacial area between the aqueous and organic phase.

An SAP catalyst is depicted in FIGS. 1A–1D. SAP catalysts generally comprise a solid support 1 possessing a surface 2 and an aqueous solution 3 containing the water soluble organometallic catalyst 4. The solid support 1 is able to immobilize the aqueous solution of the catalyst on the surface of the support. Thus, when a water soluble organometallic catalyst is introduced, the catalyst is immobilized within the aqueous solution contained on the surface of the solid support. Highly polar solvents, such as ethylene glycol, may be used in place of the aqueous solution 3 to solubilize the organometallic catalyst and to immobilize the organometallic catalyst within the SAP catalyst.

One advantage of SAP catalysts is the simplicity of catalyst recovery. When a SAP catalyst is used in a water immiscible organic solvent 5, the organometallic catalyst is retained within the aqueous solution immobilized on the surface of the solid support 1 and thus can be easily recovered by simple filtration.

The design, synthesis and use of supported aqueous phase organometallic catalysts is described in Davis, et al., U.S. Pat. No. 4,994,427, Davis, et al., U.S. Pat. No. 4,947,003, and Davis, *Chemtech* (1992) 22:498–502, each of which is incorporated herein by reference.

In order for a catalyst in a supported aqueous phase organometallic catalyst system or two phase system to be effective, the organometallic catalyst must be both soluble and active in water. In the case where a highly polar solvent, such as ethylene glycol, is used instead of water, the catalyst must be both soluble and active in the highly polar solvent.

Water solubilization of organometallic catalysts is generally performed by modifying the phosphine ligands to include highly polar functional groups such as amino, carboxylic acid, hydroxy, ether and sulfonate groups. Joo, et al., *J. Mol. Catal.* (1980) 8:369; Sinou, *Bull. Soc. Chim. Fr.* (1987) 480; Kalck, et al., *Adv. Organomet. Chem.* (1992) 34:219.

Water-soluble organometallic catalysts provide the added advantage of synthetic flexibility by enabling one to conduct reactions in an aqueous system, an organic-aqueous two phase system (Kalck, et al., *Adv. Organomet. Chem.* (1992) 34:219; Toth, et al., *Catal. Lett.* (1990) 183; Toth, et al., *Tetra. Asym.* (1990) 1:913) or as a supported aqueous phase catalyst in an organic solvent (Arhancet, et al., *Nature* (1989) 339:454; Arhancet, et al., *J. Catal.* (1990) 121:327; Arhancet, et al., *J. Catal.* (1991) 129:94; Arhancet, et al., *J. Catal.* (1991) 129:100; Davis, *Chemtech* (1992) 22:498).

Dang, et al., U.S. Pat. No. 4,654,176, describes the sulfonation of several chiral phosphines in order to render those catalysts water soluble. Dang, et al. notes that these catalysts enable reactions to be carried out in a medium comprising water and an appropriate organic solvent.

Unfortunately, sulfonation of chiral phosphine ligands has been found to result in a loss of enantioselectivity. Amrani, et al., *J. Mol. Catal.* (1984) 24:231; Lecomte, et al., *J. Organomet. Chem.* (1989) 37:277. Therefore, the need exists for an asymmetric catalyst whose enantioselectivity is not decreased when the catalyst is modified to possess greater water solubility.

A significant loss in enantioselectivity is also observed when water is used as the solvent. Toth, et al., *Tetra. Asym.* (1990) 1:913; Amrani, et al., *J. Mol. Catal.* (1984) 24:231; Sinou, et al., *J. Mol. Catal.* (1986) 36:319; Benhanza, et al., *J. Organomet. Chem.* (1985) 288:C37; Lecomte, et al., *J. Organomet. Chem.* (1989) 370:277; Oehme, et al., *J. Mol. Catal.* (1992) 71:L1. The need therefore exists for a catalyst that functions in neat water without significant loss in enantioselectivity.

SUMMARY OF THE INVENTION

The present invention relates to water soluble chiral sulfonated 2,2'-bis(diphenylphosphino)-1,1'-binaphthyl and its use as organometallic catalysts for asymmetric synthesis of optically active compounds. Asymmetric reactions of the present invention include, but are not limited to, those reactions in which organometallic catalysts are commonly used. Such reactions include reduction and isomerization reactions on unsaturated substrates and carbon-carbon bond forming reactions. Examples of such reactions include, but are not limited to, hydrogenation, hydroboration, hydrosilylation, hydride reduction, hydroformylation, alkylation, allylic alkylation, arylation, alkenylation, epoxidation, hydrocyanation, disilylation, cyclization and isomerization reactions.

The catalysts of the present invention provide the advantage of functioning in the presence of water without loss in enantioselectivity relative to the nonsulfonated BINAP catalyst in an organic solvent. As a result, the catalysts of the present invention may be employed in water, water miscible solvents, in aqueous-organic two phase solvent systems and in supported aqueous phase catalysts in organic solvents without loss in enantioselectivity. Further, the catalysts of the present invention may also be effectively employed in highly polar solvents such as primary alcohols and ethylene glycol.

The present invention also relates to a method for conducting asymmetric reactions on prochiral unsaturated bonds contained within a compound using the water soluble chiral sulfonated 2,2'bis(diphenylphosphino)-1,1'-binaphthyl organometallic catalysts of the present invention.

DETAILED DESCRIPTION OF THE PREFERRED EMBODIMENT

The present invention relates to water soluble chiral sulfonated 2,2'-bis(diphenylphosphino)-1,1'binaphthyl (BINAP-SO$_3$Na) ligands and their use as water soluble organometallic catalysts in the asymmetric synthesis of optically active compounds.

Figure 1:
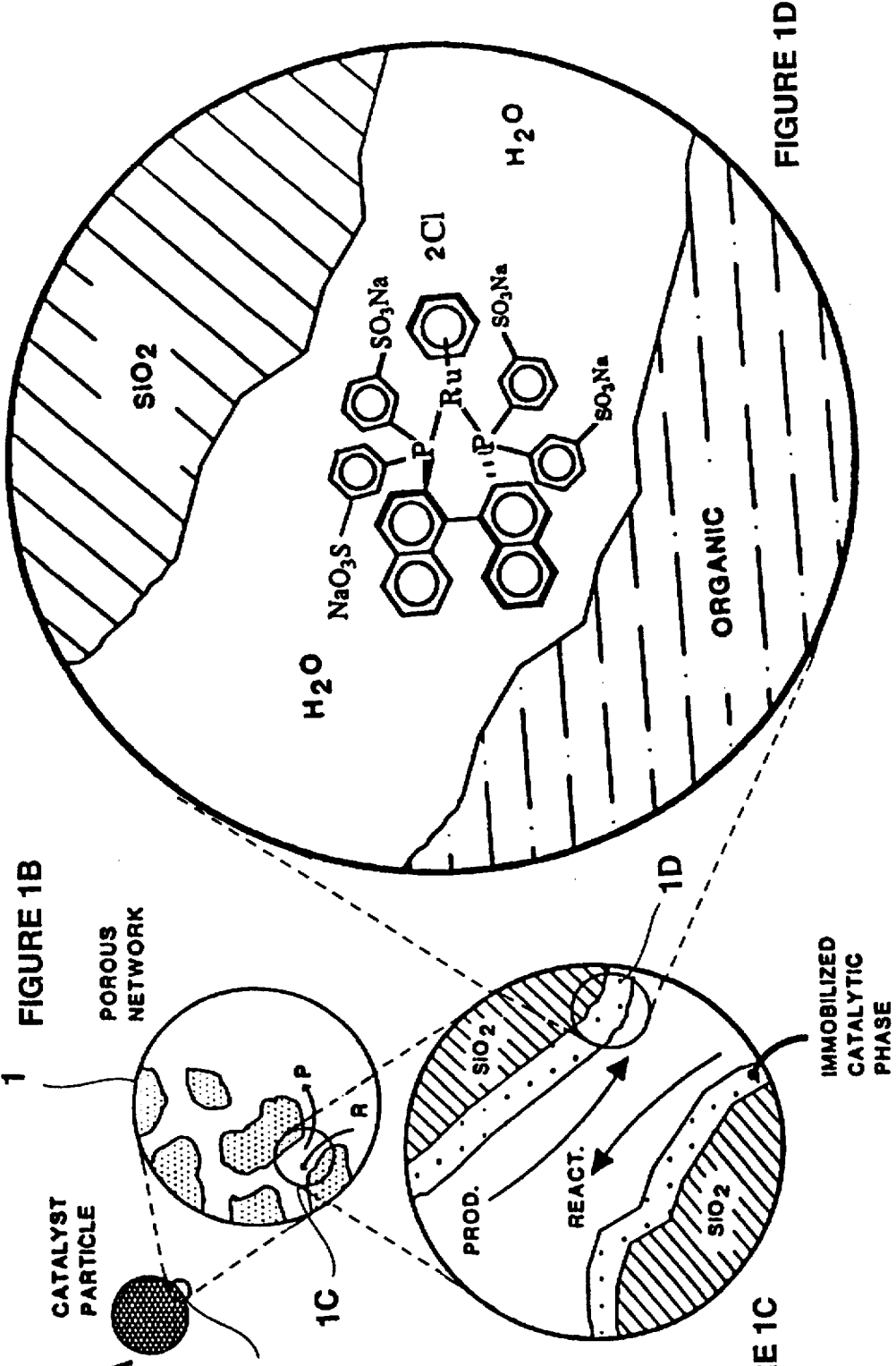
FIGS. 1A–1D depict a supported aqueous phase catalyst (SAP).
Figure 2:
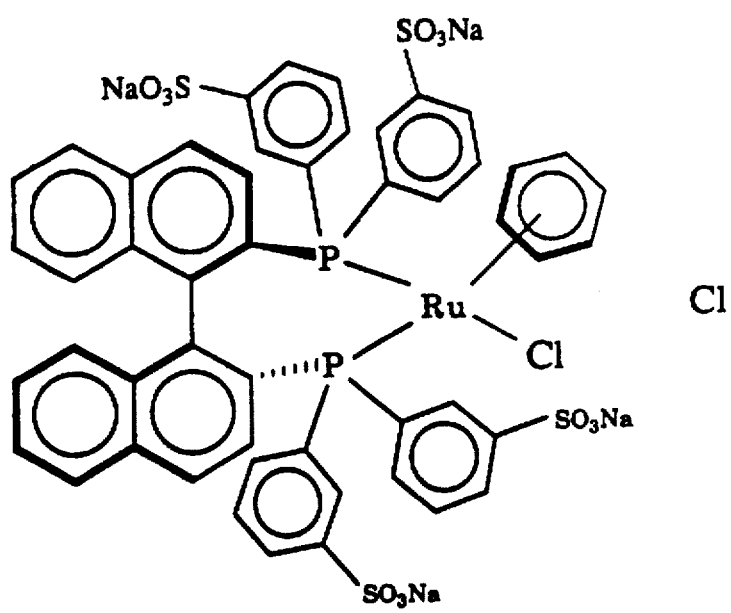
FIG. 2 depicts the preferred BINAP organometallic catalyst of the present invention, [Ru(benzene)(Cl)(BINAP-4SO$_3$Na)] Cl.

It is preferred that the chiral sulfonated binaphthyl be tetrasulfonated (BINAP-4SO$_3$Na). Metals used to form the catalysts of the present invention include those metals used in catalysts for the asymmetric reactions of the present invention. Such metals include, but are not limited to, rhodium, ruthenium, iridium, vanadium, lead, platinum, tin, nickel or palladium. With regard to hydrogenation reactions, ruthenium is the most preferred metal. It is also preferred that the catalyst comprise a counterion, most preferably Na$^+$, K$^+$, Cs$^+$ and Ca$^{2+}$. The preferred sulfonated BINAP catalyst of the present invention, [Ru(benzene)(Cl)(BINAP-4SO$_3$Na)] Cl, is depicted in FIG. 2.

Asymmetric reactions of the present invention include those reactions in which organometallic catalysts are commonly used. Such reactions include, but are not limited to, reduction and isomerization reactions on unsaturated substrates and carbon-carbon bond forming reactions. Examples of such reactions include, but are not limited to, hydrogenation, hydroboration, hydrosilylation, hydride reduction, hydroformylation, alkylation, allylic alkylation, arylation, alkenylation, epoxidation, hydrocyanation, disilylation, cyclization and isomerization reactions. In these reactions, a catalyst is generally used to catalyze the enantioselective transformation of a prochiral unsaturated substrate. Types of prochiral unsaturated substrates asymmetrically reacted using the sulfonated BINAP catalysts of the present invention include, but are not limited to, alkenes, aldehydes, ketones, thioketones, oximes, imines, enamines, allylic alcohols, allylamines and unsaturated carboxylic acids.

The present invention also relates to water soluble chiral organometallic catalysts that comprise a sulfonated BINAP ligand and a metal useful for catalyzing asymmetric reactions. Metals used to form the catalysts of the present invention include those metals used in catalysts for the asymmetric reactions of the present invention. Such metals include, but are not limited to, rhodium, ruthenium, iridium, vanadium, lead, platinum, tin, nickel or palladium.

The present invention also relates to a method for conducting an asymmetric reaction on a prochiral unsaturated bond using a water soluble organometallic catalyst that comprises a chiral sulfonated BINAP ligand of the invention.

The sulfonated catalysts of the present invention are soluble in water, water miscible solvents and highly polar solvents such as primary alcohols and ethylene glycol. The sulfonated catalysts are not soluble in nonpolar solvents such as hexane. As a result, the catalysts of the present invention may be employed in water, in the aqueous phase of an aqueous/organic two phase system, in water miscible organic solvents such as methanol, ethanol, propanol, ethylene glycol and dimethylsulfoxide as well as in water immiscible solvents where the catalyst is solubilized in an aqueous solution which is in turn immobilized on the surface of a supported aqueous phase catalyst. In each case, the sulfonated catalysts of the present invention are generally solvated by water molecules and thus catalyze asymmetric reactions in the presence of water. It should be understood that highly polar solvents, such as ethylene glycol, may be used in place of water in two phase and SAP catalyst systems.

Surprisingly, the sulfonated catalysts of the invention exhibit no significant loss in enantioselectivity in water as compared to the corresponding nonsulfonated catalyst in an organic solvent. In contrast, Amrani, et al., *J. Mol. Catal.* (1984) 24:231 and Lecomte, et al., *J. Organomet. Chem.* (1989) 370:277 teach that significant enantioselectivity is lost when sulfonated phosphine catalysts are employed in the presence of water.

As used herein, an enantioselective reaction is one where one enantiotopic face is selectively attacked over the other thereby causing the formation of one enantiomer over another. Enantiomeric excess (e.e.) is a measurement of a reaction's enantioselectivity and is defined by the quantity $$\frac{(R-S)}{(R+S)} \times 100\%$$

where R and S are relative quantities of R and S enantiomers.

The asymmetric catalysts of the present invention are preferably used in a supported aqueous phase catalyst system because of the ease of catalyst recovery and because SAP catalysts exhibit higher activity due to an increased surface area than the same catalysts in the two-phase system.

It has been observed that the enantioselectivity of the rhodium based sulfonated BINAP catalysts is not effected by the substrate concentration. This can be explained by the proposed mechanism for the substrate concentration dependent enantioselectivity of the rhodium based non-sulfonated BINAP catalyst which is depicted in FIG. 3.

Figure 3:
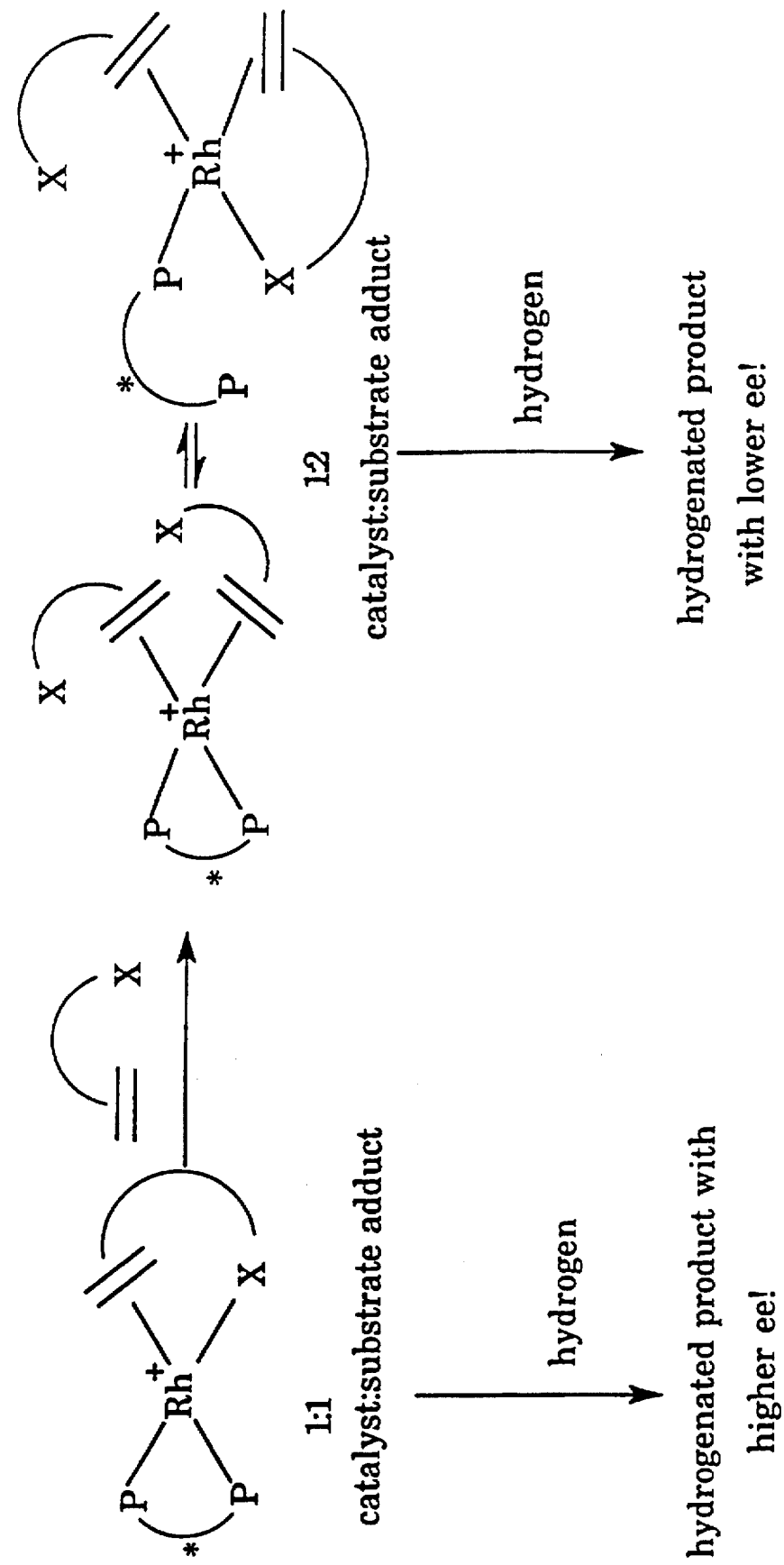
FIG. 3 depicts the mechanistic basis for enantioselectivity dependence on substrate concentration in the parent rhodium-BINAP catalyst.

As depicted in FIG. 3, when the substrate concentration is increased, the concentration of the 1:2 catalyst:substrate adduct increases. Upon hydrogenation, the 1:2 adduct produces products with decreased enantioselectivity because chelation of the substrate to the catalyst is lost and/or one of the metal-phosphorus bonds is broken upon the formation of the 1:2 adduct. This results in a decreased enantioselective interaction between the substrate and the catalyst. By contrast, it is believed that the sulfonated BINAP catalyst cannot form the corresponding 1:2 adduct due to steric hinderance caused by the sulfonate groups. This would explain why no substrate concentration effects regarding enantioselectivity are observed.

As can be seen from the data presented in Table 3, the enantioselectivity of the rhodium based sulfonated BINAP catalysts appears to increase with increases in the water concentration of the solvent. In the case of other sulfonated phosphine catalysts, decreased enantioselectivity is generally observed when the water concentration of the solvent is increased.

Ruthenium based sulfonated BINAP catalysts possess the opposite enantioselectivity as the rhodium based catalysts using the same enantiomer of the BINAP ligand. However, it should be noted that both enantiomeric products can be selectively produced using both ruthenium and rhodium based catalysts by using either the (R)- or (S)- enantiomer of the BINAP ligand. Ruthenium based sulfonated BINAP catalysts are preferred because they exhibit enantioselectivity superior to the corresponding rhodium catalysts. Further, the parent nonsulfonated ruthenium BINAP catalyst has been shown to catalyze a wider range of reactions than the corresponding nonsulfonated rhodium BINAP catalyst. Asymmetric reactions that have been conducted using the nonsulfonated ruthenium BINAP catalyst include but are not limited to hydrogenation, hydroboration, hydrosilylation, hydride reduction, hydroformylation, alkylation, allylic alkylation, arylation, alkenylation, epoxidation, hydrocyanation, disilylation, cyclization and isomerization.

The ruthenium sulfonated BINAP catalysts are also preferred because they exhibit higher stability, although less catalytic activity, than rhodium sulfonated BINAP catalysts.

The following examples set forth the synthesis and application of the chiral sulfonated BINAP catalysts of the present invention. The following examples also set forth the method by which the preferred embodiments were determined. It is understood that reactions relating to either the (R)- or (S)- BINAP catalyst can be equally employed using the other enantiomer. Therefore, specific recitation to (R)- or (S)- BINAP, or derivatives thereof, are not intended to be limiting. Further objectives and advantages of the present invention other than those set forth above will become apparent from the examples which are not intended to limit the scope of the present invention.

EXAMPLES

1. Sulfonation of (R)-BINAP under Conditions that Minimize the Formation of Phosphine Oxides and Maximize the Degree of Sulfonation Sulfonation of (R)-BINAP is preferably performed under conditions designed to eliminate the formation of phosphine oxides and to achieve a high yield of a single phosphine species. Table 1 summarizes the results from sulfonating (R)-BINAP under a variety of reaction conditions.

TABLE 1

| [SO₃]% | Time (days) | Temp. (°C.) | Products* |
|---|---|---|---|
| 30 | 5 | 22 | 55% mixture of sulfonated products + 45% oxides |
| 30 | 4 | 50 | 100% oxides |
| 25 | 3 | 0 | 100% oxides |
| 50 | 5 | <10 | 70% mixture of sulfonated products 30% oxides |
| 43 | 4.5 | 10 | single major sulfonated product + 5% oxides |
| 40 | 3 | 0 | single major sulfonated product |

*(based on $^{31}$P NMR signals)

Based on the test results summarized in Table 1, the following sulfonation protocol was designed in order to minimize the formation of phosphine oxides and to selectively produce the tetra-sulfonated BINAP derivative. First, 1 g of (R)-BINAP was dissolved in 3.5 ml of concentrated sulfuric acid at 10° C. under argon. Afterward, 15 ml of fuming sulfuric acid (40 wt % sulfur trioxide in concentrated sulfuric acid) was added dropwise over 2–3 hours. The resulting solution was then stirred at 10° C. under an argon atmosphere for 3 days. In the event that the reaction mixture solidifies, it is preferred that a stepwise addition of sulfur trioxide be used rather than a dropwise addition in order to prevent solidification.

After stirring, the reaction was quenched by pouring the sulfuric acid solution into 100 ml of ice cooled water followed by the dropwise addition of 50 wt % NaOH until the solution was neutralized to pH 7. The resulting aqueous solution was then reduced to 30 ml under vacuum. 100 ml of methanol was then added to the concentrated solution in order to precipitate any sodium sulfate present in solution.

The sodium sulfate was removed by filtration and the supernatant reduced under vacuum to yield a solid. The solid was then dissolved in neat methanol to remove trace amounts of sodium sulfate to yield sulfonated (R)-BINAP in a 70–75% yield.

Complete removal of sodium sulfate was confirmed by $^{33}$S NMR. The presence of sodium sulfate in the isolated solid was measured by oxidizing the sample followed by analyzing the sample using $^{33}$S NMR in D$_2$O. No sodium sulfate was detected after 150,000 NMR scans. No further information regarding the sample's composition could be obtained due to the fact that the sulfate groups on the sulfonated BINAP give a broad peak around −13 ppm relative to ammonium sulfate.

Elemental analysis of the resulting product indicated that it was approximately 85% tetrasulfonated BINAP (BINAP-4 SO$_3$Na: Calculated S/P:Na/P:C/Na=2:2:11; Found S/P:Na/P:C/Na=2.34:2.02:11.31). The product was then analyzed by $^{31}$P NMR which showed a single major resonance at −11.1 ppm and a second smaller resonance at −12.7 ppm (relative to H$_3$PO$_4$), the two resonances having intensity ratios of 86:14. The presence of a single major $^{31}$P resonance indicates that the product is symmetrical about each phosphorous atom. Equivalent phosphorous atom resonances would be expected if each phenyl ring of the BINAP ligand is sulfonated, thereby creating a symmetrical molecule. Thus, it is believed that each phenyl ring of the BINAP ligand is monosulfonated.

It is believed that sulfonation occurs on the phenyl rings rather than the naphthyl rings due to a difference in the π-stabilization energy of the aromatic rings, thereby causing the phenyl rings to be more reactive toward electrophilic aromatic substitution by sulfur trioxide than the naphthyl rings. This hypothesis is supported by the observation of a single major $^{31}$p NMR signal. At least two NMR resonances having equal intensities would appear in the $^{31}$p spectrum of a tetra-sulfonated BINAP if the naphthyl ring was also sulfonated. Nonetheless, definitive assignments are not possible due to the complexity of the $^1$H and $^{13}$C NMR spectra.

It is believed that the second minor NMR resonance observed corresponds to penta- and hexa-sulfonated BINAP derivatives where the additional sulfonate groups appear on the naphthyl rings. Production of higher sulfonated BINAP derivatives is not expected to adversely impact enantioselectivity since enantioselectivity is believed to be based on the interaction of the phenyl rings with the substrate and not the naphthyl rings. The observation of similar activity and selectivity between separately prepared batches of ligands having different major to minor species ratios appears to confirm the hypothesis that enantioselectivity is not adversely affected by sulfonation of the naphthyl rings.

2. Preparation of Rhodium BINAP-4 SO$_3$Na Catalyst

The rhodium BINAP-4 SO$_3$Na catalyst was prepared by reacting [Rh(COD)Cl]$_2$, wherein COD represents cycloocta-1,5-diene, with two equivalents of (R)-BINAP-4SO$_3$Na in water at room temperature in the presence of excess sodium perchlorate to form the cationic species [Rh[(R)-BINAP-4 SO$_3$Na](COD)](ClO$_4$). Exposure of [Rh[(R)-BINAP-4 SO$_3$Na](COD)](ClO$_4$) to one atmosphere of dihydrogen yields the active catalyst [Rh[(R)-BINAP-4 SO$_3$Na] (H$_2$O)$_2$]$^+$. The rhodium BINAP-4 SO$_3$Na catalyst may also be prepared in methanol to yield the active catalyst [Rh[(R)-BINAP-4 SO$_3$Na] (methanol)$_2$]$^+$. Further addition of two equivalents of (R)-BINAP-4 SO$_3$Na or the initial admixture of four equivalents of [Rh(COD)Cl]$_2$ yields the inactive complex [Rh[(R)-BINAP-4 SO$_3$Na]$_2$]$^+$. Assignments for these species are based on the data presented in Table 2.

TABLE 2

$^{31}$P NMR data for various ligands and rhodium complexes

| Compound | Solvent | δ(ppm)[1] | J$_{Rh-p}$(Hz) |
|---|---|---|---|
| BINAP-4SO$_3$Na(L) | D$_2$O | −11.0(s) | — |
| [Rh(L)COD]ClO$_4$ | D$_2$O | 31.0(d) | 144 |
| [Rh(L)(D$_2$O)$_2$]ClO$_4$ | D$_2$O | 51.0(d) | 196 |
| (S)-BINAP (L') | C$_6$D$_6$:CD$_3$OD(4:1) | −12.8(s) | — |
| [Rh(L')(NBD)]ClO$_4$ | CD$_3$OD | 25.1(d) | 156 |
| [Rh(L')(CH$_3$OH)$_2$]ClO$_4$ | CD$_3$OD | 53.1(d) | 206 |
| (S,S)-cyclobutanediop-(L'')-4SO$_3$Na | D$_2$O | −20.2(s) | — |
| [Rh(COD)Cl]$_2$+(L'') | D$_2$O | 20.2(d) | 144 |
| [Rh(L'')(H$_2$O)$_2$]$^+$ | D$_2$O | 43.5(d) | 182 |
| (S,S)-BDPP(L''')-4So$_3$Na | D$_2$O | 0.7(s) | — |
| [Rh(COD)Cl]$_2$+L''' | D$_2$O | 29.3(d) | 144 |
| [Rh(L''')(H$_2$O)$_2$]$^+$ | D$_2$O | 53.2(d) | 185 |

[1] $^{31}$P NMR chemical shifts relative to 85 wt % H$_3$PO$_4$; downfield shifts are positive.

3. Asymmetric Hydrogenation of 2-Acetamidoacrylic acid and methyl-2-acetamidoacrylate Using [Rh[(R)-BINAP-4 SO$_3$Na] (H$_2$O)$_2$]$^+$ Asymmetric hydrogenation of 2-acetamidoacrylic acid and methyl-2-acetamidoacrylate using [Rh[(R)-BINAP-4 SO$_3$Na] (H$_2$O)$_2$]$^+$ was conducted at room temperature and one atmosphere of dihydrogen in batch autoclaves. Hydrogenation of the alkene was measured by $^1$H NMR. The enantiomeric excesses of the products were determined by first derivatizing the amino acids to N-trifluoroacetyl amino acids according to El Baba, et al., *Tetrahedron* (1984) 40:4275. The resulting N-trifluoroacetyl amino acids were then separated and analyzed by gas chromatography using a J & W Scientific CDX B chiral capillary column.

As depicted in Table 3, the (S) enantiomers of 2-acetamidoacrylic acid and methyl-2-acetamidoacrylate are preferentially formed using the [Rh[(R)-BINAP-4 SO$_3$Na] (H$_2$O)$_2$]+ catalyst. Hence, [Rh[(R)-BINAP-4 SO$_3$Na] (H$_2$O)$_2$]+ provides the same enantioselectivity as the non-sulfonated rhodium BINAP catalyst. Miyashita, et al., *Tetrahedron* (1984) 40:1245.

TABLE 3

Reduction of 2-acetamidoacrylic acid and methyl-2-acetamidoacrylete using {Rh[(R)-BINAP-4SO$_3$Na] (solvent)$_2$} (ClO$_4$) at room temperature under 1 atm. of H$_2$

| Substrate | Solvent | Conc. (M) | ee(%) |
|---|---|---|---|
| 2-acetamidoacrylic acid | methanol | 0.078 | 58.0 |
| " | " | 0.017 | 58.0 |
| " | " | 0.003 | 57.5 |
| " | " | 0.007 | 70.4 |
| methyl-2-acetamidoacrylate | " | 0.134 | 50.8 |
| " | " | 0.017 | 47.8 |
| " | " | 0.003 | 49.0 |
| " | water | 0.039 | 68.8 |
| " | " | 0.017 | 68.5 |

Unexpectedly, the sulfonated BINAP catalyst exhibits roughly the same enantioselectivity in neat water (70.4–68.0%) as was observed by A. Miyashita, et al. using the unsulfonated BINAP catalyst in ethanol (67.0%).

Miyashita, et al., *Tetrahedron* (1984) 40:1245. This is surprising since sulfonation of phosphine ligands generally results in a loss of enantioselectivity.

The sulfonated rhodium BINAP catalysts of the present invention are further distinguishable from the corresponding non-sulfonated BINAP catalysts by the fact that enantioselectivity is substrate concentration independent as shown by the data presented in Table 3.

Without being bound by theory, the observed substrate concentration independence is believed to be due to the bulky sulfonated phenyl rings of the BINAP ligand which inhibit the formation of a 1:2 catalyst:substrate adduct. As depicted in FIG. 3, enantioselectivity is lost when a 1:2 catalyst:substrate adduct forms. When the phenyl rings of the BINAP ligand are not sulfonated, there is less steric hinderance to prevent the formation of a 1:2 catalyst:substrate adduct. Thus, at higher substrate concentrations, the population of the 1:2 catalyst:substrate adduct increases and results in lower enantioselectivity. By contrast, the added steric bulk created by the sulfonate groups on the phenyl rings inhibits the formation of the 1:2 catalyst:substrate adduct at higher substrate concentrations. As a result, the enantioselectivity of the sulfonated catalysts of the present invention exhibits substrate concentration independence.

The substrate concentration independence of the sulfonated catalysts of the present invention enable the use of these catalysts to be scaled up because increases in substrate concentration do not adversely impact enantioselectivity. By contrast, scale-up using the non-sulfonated BINAP catalyst has been limited by the adverse impact increases in substrate concentration have on enantioselectivity.

In addition to exhibiting enantioselectivity that is substrate concentration independent and showing the same enantioselectivity in neat water as the unsulfonated BINAP catalyst in ethanol, the sulfonated rhodium BINAP catalysts of the present invention also do not exhibit the same loss in enantioselectivity that is generally observed when water is used as a solvent. As shown in Table 4, the enantioselectivity of the sulfonated rhodium BINAP catalysts of the present invention actually increases with increases in the water concentration. The same trend in enantioselectivity was observed using both 2-acetamidoacrylate and its corresponding methyl ester as substrates. As can be seen from the data in Table 4, the enantioselectivity of the sulfonated rhodium BINAP catalysts of the present invention when used in water is contrary to the enantioselectivity prior art sulfonated chiral catalysts.

TABLE 4

| Substrate | Solvent | Conc. (M) | ee % |
|---|---|---|---|
| $Rh[(R)-BINAP-4SO_3Na](solvent)_2(ClO_4)$ | | | |
| 2-acetamidoacrylic acid | water | 0.007 | 70.4(S) |
| " | 7:1 water/methanol | 0.017 | 67.0(S) |
| " | 1:1 water/methanol | 0.017 | 56.0(S) |
| " | 1:2 water/methanol | 0.042 | 55.0(S) |
| " | methanol | 0.017 | 58.0(S) |
| methyl-2-acetamidoacrylic acid | water | 0.017 | 68.5(S) |
| " | 4:2 water/methanol | 0.017 | 61.2(S) |
| " | 1:1 water/methanol | 0.017 | 42.1(S) |
| " | methanol | 0.017 | 47.8, 47.3(S) |
| $[Rh(R-BINAP)(solvent)_2]^+$ | | | |
| methyl-2-acetamidoacrylic acid | ethanol | N.R. | 67.0* |
| $[Rh(COD)1A](ClO_4)‡$ | | | |
| acetamidocinnamic acid | methanol | 0.1 | 80.0(S) |
| " | 1:9 water/methanol | 0.1 | 75.5(S) |
| " | 3:7 water/methanol | 0.1 | 70.0(S) |
| " | 1:1 water/methanol | 0.1 | 63.5(S) |
| " | ethanol | 0.1 | 82.0(s) |
| " | 1:4 water/ethanol | 0.1 | 77.0(S) |
| " | 2:3 water/ethanol | 0.1 | 75.0(S) |
| " | 3:2 water/ethanol | 0.1 | 70.0(S) |
| methyl-acetamidocinnamic acid | methanol | 0.1 | 50.0(S) |
| " | 1:9 water/methanol | 0.1 | 47.0(S) |
| " | 3:7 water/methanol | 0.1 | 40.0(S) |
| " | 1:1 water/methanol | 0.1 | 35.0(S) |
| " | 7:3 water/methanol | 0.1 | 27.0(S) |
| $[Rh(COD)2B](ClO_4)‡$ | | | |
| acetamidocinnamic acid | ethanol | 0.1 | 73.0(S) |
| " | 3:17 water/ethanol | 0.1 | 70.0(S) |
| " | 1:3 water/ethanol | 0.1 | 68.0(S) |
| " | 1:1 water/ethanol | 0.1 | 63.0(s) |
| " | 4:1 water/ethanol | 0.1 | 43.0(S) |
| " | water | 0.1 | 33.0(S) |

N.R. = not reported.
*Miyashita, et al., Tetrahedron (1984) 40:1245.
‡Data for these catalysts from Lecomte, et al., J. Organomet. Chem. (1989) 370:277.

TABLE 4-continued

| Substrate | Solvent | Conc. (M) | ee % |
|---|---|---|---|

[1] cyclobutane with PAr$_2$, PAr$_2$ substituents

[2] chain with PAr$_2$, PAr$_2$ substituents (A) Ar = phenyl (B) Ar = phenyl-SO$_3$Na

4. Comparison of Initial Turnover Rates of Sulfonated and Nonsulfonated Catalysts Comparison of the turnover rates of sulfonated and non-sulfonated (R-BINAP) rhodium catalysts is set forth in Table 5. A significant decrease in the catalyst turnover rate is observed when water is used as the solvent. This is believed to be due to the lower solubility of dihydrogen in water. The solubility of dihydrogen in ethanol and water at 25° C. at 1 atm. is $38.2 \times 10^{-4}$M and $8.53 \times 10^{-4}$M respectively. Despite the lower turnover rate, reasonable activity in neat water is achieved under mild reaction conditions (room temperature, 1 atm).

TABLE 5

| Catalyst | Solvent | Turnover (hr$^{-1}$) | ee (%)* |
|---|---|---|---|
| [Rh[(R)-BINAP-4SO$_3$Na](solvent)$_2$](ClO$_4$) | water | 41 | 69 |
| [Rh[(R)-BINAP-4SO$_3$Na](solvent)$_2$](ClO$_4$) | ethanol | 302 | 56 |
| [Rh[(R)-BINAP](solvent)(ClO$_4$)THF[b] | ethanol | 389 | 20 |
| [Rh[(R)-BINAP](solvent)(ClO$_4$) | ethanol | 467 | 22 |
| [Rh[(R)-BINAP](solvent)(ClO$_4$)THF[b,c] | ethanol | 264 | 35 |
| [Rh[(R)-BINAP-4SO$_3$Na](solvent)$_2$](ClO$_4$) | water | 45 | 68 |

Substrate: methyl-2-acetamidoacrylate
Conditions: T = 23° C.; P = 1 atm
[a][substrate]/[Rh] = 76; chemical yield quantitative
[b]from Aldrich
[c]2-acetamidoacrylic acid as substrate
[d]from a different batch of ligand
*at 100% conversion

5. Preparation of Ruthenium BINAP-4 SO$_3$Na Catalyst

The ruthenium BINAP-4 SO$_3$Na catalyst was prepared by reacting [Ru(benzene)Cl$_2$]$_2$ with two equivalents of (R)-BINAP-4SO$_3$Na in a 1:8 benzene/methanol solvent to yield [Ru(benzene)Cl[(R)-BINAP-4 SO$_3$Na]]Cl. $^{31}$p NMR (CD$_3$OD): d.d. δ=63.0, δ 68.8 ppm J=45 Hz. Specifically, 0.001 g of [Ru(benzene)Cl$_2$]$_2$ was stirred with 0.0050 g BINAP-SO$_3$Na in 4.5 ml of a 1:8 benzene/methanol solvent at 55° C. under argon for 1-2 hours. The resulting solution was then vacuum dried at room temperature.

Interestingly, reacting [Ru(benzene)Cl$_2$]$_2$ with two equivalents of (R)-BINAP-4SO$_3$Na in water at 55°–60° C. for 2 hours did not yield a highly active catalyst for hydrogenation. The $^{31}$p NMR spectrum of the resulting product contained two peaks in strictly a 1:1 ratio [$^{31}$p NMR (D$_2$O): d=57.5 and 63.7 ppm]. From the difference in line shape, the two resonances appear to be originating from different phosphorous atoms. A $^2$Jpp coupling could not be observed in water. Because P—C bond cleavage of Rh-phosphine complexes is well known (Abatjoglou, et al., *Organometallics* (1984) 3 923), it is speculated that a similar oxidative addition of the phosphorous-naphthyl bond to the Ru center is occurring. Since the oxidative addition of a P—C bond from a phosphine to a transition metal center is promoted by the presence of a vacant coordination site, a weakly coordinating agent, such as an aromatic solvent, can be used to suppress oxidation addition of a P—C bond.

6. Asymmetric Hydrogenation Using ruthenium (R) -BINAP Catalyst

Asymmetric hydrogenation of 2-acetamidoacrylic, methyl-2-acetamidoacrylate and 2-acetamidocinnamic acid was performed using the sulfonated ruthenium BINAP catalysts prepared according to Example 5. The results of the hydrogenation are set forth in Table 6.

TABLE 6

| Substrate | Solvent | Pressure | T(°C.) | ee% |
|---|---|---|---|---|
| Ru$_2$Cl$_4$(BINAP)$_2$(Et$_3$N) | | | | |
| 2-acetamidoacrylic acid | 1:1 ethanol-THF | 2 | 35 | 76.0(R)$^1$ |
| 2-acetamidocinnamic acid | ethanol/THF/Et$_3$N | 1 | RT | 86.0(S) |
| [Ru (benzene) (BINAP-4SO$_3$Na)]$^{2+}$ | | | | |
| 2-acetamidoacrylic acid | methanol | 1 | RT | 84.2(R) |
| 2-acetamidoacrylic acid | water | 1 | RT | 68.5(R) |
| methyl-2-acetamido-acrylic acid | methanol | 1 | RT | 84.7(R) |

TABLE 6-continued

| Substrate | Solvent | Pressure | T(°C.) | ee% |
|---|---|---|---|---|
| methyl-2-acetamido-acrylic acid | water | 1 | RT | 75.9(R) |
| methyl-2-acetamido-acrylic acid | water | 1 | 50 | 82.0(R) |
| 2-acetamidocinnamic acid | methanol | 1 | RT | 81.3(R) |
| 2-acetamidocinnamic acid | 1:1 methanol:water | 1 | RT | 84.0(R) |
| 2-acetamidocinnamic acid | water | 1 | RT | 87.7(R) |
| 2-acetamidocinnamic acid | ethanol | 1 | RT | 80.1(R) |

[1]Data from Kawano, et al., J.C.S. Perkin Trans. I, (1989) 1571.

As can be seen from the results depicted in Table 6, the ruthenium catalysts of the present invention possess the opposite enantioselectivity as rhodium based sulfonated BINAP catalysts using the same BINAP enantiomer. The data from Table 6 also indicates that the enantioselectivity of ruthenium based sulfonated BINAP catalysts, unlike the rhodium catalysts, varies with regard to water concentration dependence, depending on the substrate used. For example, with 2-acetamidocinnamic acid, enantioselectivity increases with increases in water concentration. By contrast, enantioselectivity with 2-acetamidoacrylic acid decreases with increases in water concentration.

7. Asymmetric Hydrogenation Using Ruthenium Sulfonated BINAP Catalyst in Methanol In contrast to most other sulfonated phosphine systems, (Amrani, et al. *Organometallics* (1989) 8:542; Bartik, et al. *Organometallics* (1993) 12:164) the ruthenium sulfonated BINAP catalyst is quite soluble in neat methanol. Methanol is known to give the highest enantiomeric excess in many of the asymmetric reactions catalyzed by non-sulfonated complexes.

Asymmetric hydrogenation of 2-(6'-methoxy-2'-naphthyl)acrylic acid by the non-sulfonated Ru-BINAP catalyst has been carried out in neat methanol. Chan, et al. in "Selectivity In Catalysis" (Davis, M. E., and Suib, S. L., Eds.) Chap. 3, p. 27. *ACS Symposium Series* 517 (1993). Homogeneous, asymmetric hydrogenations of 2-(6'-methoxy-2'-naphthyl)acrylic acid were conducted in methanolic solvents to allow a direct comparison between the sulfonated and parent system.

Reductions were carried out under a hydrogen pressure of 500-1400 psig. In neat methanol, the sulfonated BINAP catalyst (96.1% at 4° C.) was found to be as enantioselective as the corresponding nonsulfonated BINAP catalyst (96.0% at 0° C.), at slightly higher hydrogen pressure.

8. Asymmetric Hydrogenation in Two Phase Solvent System

Hydrogenation in a simple two-phase reaction system was performed in order to compare catalyst performance with results using a homogeneous solvent system as well as a SAP catalyst. Anhydrous ethyl acetate was chosen as the organic solvent. 2-(6'-methoxy-2'-naphthyl) acrylic acid was used as the substrate. When the substrate was charged into the hydrogenation reactor along with an aqueous solution of the ruthenium catalyst (10 ml of 1:1 ethyl acetate/water and S/C=50), a 53.6% conversion was observed in 3.5 days with an initial turnover frequency of 0.34hr$^{-1}$. Table 7, Entry 1. In comparison to neat methanol, the two-phase reaction system is at least 350 times slower. Table 7, Entry 1 and 13.

The slower reaction rate is most likely due to the limited solubility of the substrate in water. As a result, most of the reaction is taking place at the aqueous-organic phase interface. The rate is therefore limited by the interfacial surface area between the catalyst containing aqueous phase and the substrate containing organic phase. As will be discussed in Section 9, the surface area limitation of two phase systems is significantly reduced by using a SAP catalyst which has been found to be 50 times more active than the two phase system. This is due to the much larger interfacial surface area provided by the high surface area SAP solid support.

TABLE 7

| Entry | Solvent | S/C[a] | Hydrogen Pressure (psig) | Conv. (%) | T.O.F. (hr$^{-1}$)[b] | e.e. (%) |
|---|---|---|---|---|---|---|
| 1 | 1:1 ethyl acetate/H$_2$O | 50 | 1380 | 53.6 | 0.34 | 78.4 |
| 2 | 1:1 ethyl acetate/H$_2$O | 25 | 1360 | 56.7 | — | 81.1 |
| 3 | 1:1 ethyl acetate/H$_2$O | 25 | 1360 | 56.4 | — | 70.0[c] |
| 4 | 1:1 ethyl acetate/H$_2$O | 25 | 1370 | 57.0 | — | 82.7[d] |
| 5 | 1:1 ethyl acetate/H$_2$O | 15 | 1365 | 90.0 | 0.20 | 77.2[e] |
| 6 | 1:1 ethyl acetate/H$_2$O | 14 | 1320 | 100.0 | — | 73.0[f] |

[a]substrate to ruthenium ratio
[b]initial turnover frequency
[c]aqueous solution recycled once
[d]aqueous solution recycled twice
[e]reaction temperature = 5° C.
[f]with added triethylamine, Et$_3$N/substrate = 1

TABLE 7 Part 2

| Entry | Solvent | S/C[a] | Hydrogen Pressure (psig) | Conv. (%) | T.O.F. (hr$^{-1}$)[b] | e.e. (%) |
|---|---|---|---|---|---|---|
| 7 | MeOH | 50 | 1370 | N/A | — | 86.0(R) |
| 8 | MeOH | 53 | 500 | N/A | — | 84.7(R) |
| 9 | 1:1 MeOH/H$_2$O | 25 | 1320 | N/A | — | 78.9(R) |
| 10 | 1:1 MeOH/H$_2$O | 25 | 1340 | N/A | — | 75.1(R)[d] |
| 11 | MeOH | 25 | 1370 | N/A | — | 89.5(R)[d] |
| 12 | MeOH | 25 | 1360 | N/A | — | 91.0(R)[d] |
| 13 | MeOH | 101 | 1350 | N/A | 131 | 88.2(R) |
| 14 | MeOH | 101 | 1350 | N/A | 927 | 91.5(R)[d] |
| 15 | MeOH | 51 | 1370 | N/A | — | 86.2(R)[e] |
| 16 | 1:1 MeOH/H$_2$O | 51 | 1320 | N/A | — | 75.7(R)[e] |
| 17 | 1:1 MeOH/H$_2$O | 50 | 1350 | N/A | 0.77[f] | — |
| 18 | 1:1 MeOH/H$_2$O | 52 | 1350 | N/A | — | 77.6(R)[g] |
| 19 | MeOH | 52 | 500 | N/A | — | 87.5(R)[d] |
| 20 | MeOH | — | 500 | N/A | — | 93.3(R)[d,h] |
| 21 | MeOH | 100 | 1230 | N/A | — | 96.1(R)[d,i] |
| 22 | MeOH | — | 500 | N/A | — | 96.0(R)[d,h,j] |

[a]substrate to ruthenium ratio
[b]initial turnover frequency
[c]e.e. determined at 100% conversion
[d]with added triethylamine, Et$_3$N/substrate = 1
[e]with added sodium 3-pyridinesulfonate, m-SO$_3$Na-pyridine/substrate = 1
[f]with added concentrated sulfuric acid in 10 times excess of substrate
[g]with added tetrahydrofuran in 1.9 times excess of substrate
[h]Chan, et al., "Selectivity in Catalysis," M. E. Davis and S.L. Snib, Eds. ACS Symposium Series 517 (1993)
[i]reaction temperature = 4° C.
[j]reaction temperature = 0° C.

Because of the limited solubility of the substrate in water, we cannot rule out the possibility that a small portion of the conversion is by reaction in the bulk aqueous phase. A 78.4% e.e. was obtained from the two-phase reaction. As shown by entries 2, 3 & 4 of Table 7, recycling of the catalyst containing aqueous phase after phase separation is possible without any drop in enantioselectivity. The enantioselectivity ranged from 78.0–82.7% over several recycles of the catalytic solution. Similar enantioselectivity but lower activities ($0.20hr^{-1}$) were found at a reaction temperature of 5°–6° C. Table 7, Entry 5.

9. Asymmetric Hydrogenation Using a Supported-Aqueous-Phase Catalyst

In the supported-aqueous-phase configuration, anhydrous ethyl acetate is used as the organic phase. Catalytic data obtained using the sulfonated BINAP catalyst in a SAP system is listed in Tables 8 and 9. The turnover rates of the SAP catalysts were significantly higher than the two-phase system. This is believed to be due to the much higher contact surface area of the SAP catalysts. When 2-(6'-methoxy-2'-naphthyl) acrylic acid was hydrogenated with a "dried" sample of the SAP catalyst (1.9 wt % water), no detectable conversion is observed even after 70 hours at room temperature under 1300 psig of hydrogen pressure (T.O.F.<$0.008hr^{-1}$). Table 9, Entry 1. Significantly, when water-saturated ethyl acetate was used as solvent, a 100% conversion (S/C=31.5) was achieved in ~3 hours under the same reaction conditions with an initial turnover frequency of $18.2hr^{-1}$ and up to an 70% e.e. Table 8, Entry 5, Table 9, Entry 8. This enantioselectivity is only slightly lower than that found in the water-organic two-phase system where the only difference is in the contact surface area between the aqueous phase and the organic phase.

Similar results were also observed from other batches of SAP catalysts. Table 8, Entries 2, 6 & 9. Additionally, the enantiomeric excess of the hydrogenated product when using a SAP catalyst with 40 µl water in 10 ml of ethyl acetate as the organic solvent was found to be only 28.7% (R). Table 8, Entry 1.

Based on the results presented in Tables 8 and 9, it is evident that the water content in the SAP catalyst has a dramatic affect on both catalyst activity and enantioselectivity. It is therefore important to have a means for rehydrating the catalyst. Vapor-phase impregnation of water onto the SAP solid support is not feasible for the present system since the ruthenium-sulfonated-BINAP catalyst is not as hydrophilic as the rhodium-TPPTS catalyst developed by Wan, K. T., et al. *J. Catal.* (in press); Arhancet, et al. *Nature* (1989) 339:454; Arhancet, et al. *J. Catal.* (1990) 121:327. The revised method of in-situ rehydration by water-loaded blank support also requires higher reaction temperature (80°–100° C.) for the re-distribution of water over the SAP catalyst. Arhancet, et al. *J. Catal.* (1991) 129:94. This approach for loading water into the SAP catalyst is also not possible.

TABLE 8

Heterogeneous, asymmetric hydrogenation of 2-(6'-methoxy-2'-naphthyl) acrylic acid by SAP-Ru-BINAP-4SO$_3$Na catalyst in ethyl acetate

| Entry | Cycle[a] | Solvent | S/C[b] | Hydrogen Pressure (psig) | Stirring Speed (rpm) | e.e (%) |
|---|---|---|---|---|---|---|
| 1 | 0 | AcOEt (40µlH$_2$O) | 25 | 1300 | 350 | 28.7 (R) |
| 2 | 0 | AcOEt (H$_2$O sat.) | 33 | 1300 | 350 | 69.0 (R)[c] |

TABLE 8-continued

Heterogeneous, asymmetric hydrogenation of 2-(6'-methoxy-2'-naphthyl) acrylic acid by SAP-Ru-BINAP-4SO$_3$Na catalyst in ethyl acetate

| Entry | Cycle[a] | Solvent | S/C[b] | Hydrogen Pressure (psig) | Stirring Speed (rpm) | e.e (%) |
|---|---|---|---|---|---|---|
| 3 | 1 | AcOEt (H$_2$O sat.) | 30 | 500 | 350 | 68.3 (R) |
| 4 | 1 | AcOEt (H$_2$O sat.) | 25 | 1330 | 350 | 68.6 (R)[c] |
| 5 | 2 | AcOEt (H$_2$O sat.) | 25 | 1330 | 350 | 70.0 (R)[c] |
| 6 | 0 | AcOEt (H$_2$O sat.) | 30 | 1360 | 300 | 67.0 (R) |
| 7 | 1 | AcOEt (H$_2$O sat.) | 30 | 1360 | 300 | 67.0 (R) |
| 8 | 2 | AcOEt (H$_2$O sat.) | 31 | 1360 | 300 | 66.0 (R) |
| 9 | 0 | AcOEt (H$_2$O sat.) | 30 | 1330 | 500 | 69.0 (R) |
| 10 | 1 | AcOEt (H$_2$O sat.) | 30 | 1250 | 500 | 65.0 (R) |
| 11 | 2 | AcOEt (H$_2$O sat.) | 30 | 1050 | 550 | 66.0 (R) |
| 12 | 3 | AcOEt (H$_2$O sat.) | 30 | 1260 | 350 | 77.0 (R)[d] |
| 13 | 5 | AcOEt (H$_2$O sat.) | 31 | 1360 | 350 | 62.8 (R)[e] |
| 14 | 6 | AcoEt (H$_2$O sat.) | 30 | 1350 | 350 | 63.6 (R) |
| 15 | 7 | AcOEt (H$_2$O sat.) | 30 | 1370 | 350 | 64.6 (R)[e,a] |
| 16 | 0 | AcOEt (200µl-NaOH) | 30 | 1380 | 350 | 62.8 (R)[f] |
| 17 | 1 | AcOEt (NaOH sat.) | 30 | 1380 | 350 | 59.9 (R)[f] |
| 18 | 2 | AcOEt (NaOH sat.) | 30 | 1000 | 350 | 59.8 (R)[f] |
| 19 | 3 | AcOEt (NaOH sat.) | 30 | 500 | 350 | 58.6 (R)[f] |
| 20 | 4 | AcOEt (H$_2$O sat.) | 30 | 1350 | 350 | 62.7 (R) |

[a]number of catalyst recycles
[b]substrate to ruthenium ratio
[c]no ruthenium found in the filtrate with a detection limit of 1 ppm
[d]reaction temperature = 8° C.
[e]with added triethylamine, Et$_3$N/substrate = 1
[f]with 0.22 M sodium hydroxide solution

TABLE 9

Catalytic activity as a function of water content in the heterogeneous, asymmetric hydrogenation of 2-(6'-methoxy-2'-naphthyl) acrylic acid by SAP-Ru-BINAP-4SO$_3$Na catalyst in ethyl acetate.

| Entry | S/C[a] | Hydrogen Pressure (psig) | Water Content (µl)[b] | T.O.F. (Hr$^{-1}$)[c] |
|---|---|---|---|---|
| 1 | 33 | 1330 | 0 | <0.008 |
| 2 | 25 | 1130 | 40 | 0.22 |
| 3 | 30 | 1350 | 125 | 0.25[d] |
| 4 | 30 | 1360 | 145 | 1.06[d] |
| 5 | 31 | 1370 | 160 | 2.35[d] |
| 6 | 30 | 1400 | 195 | 2.84[d] |
| 7 | 30 | 1370 | 215 | 5.12[d] |
| 8 | 32 | 1370 | 270 (saturated) | 18.21[d] |

[a]substrate to ruthenium ratio
[b]hydrogenations were carried out in 10 ml of ethyl acetate at room temperature and with 350 rpm stirring speed, [substrate] = 4.6–4.8 × $10^{-3}$M
[c]initial turnover frequency
[d]no ruthenium found in the filtrate with a detection limit of 1 ppm.

Organic-phase impregnation was developed as a rehydration procedure. This process is more feasible for sulfonated BINAP SAP catalysts, especially in terms of scale-up. Organic-phase impregnation is accomplished by rehydrating "dried" SAP catalyst that has been previously premixed with a controlled amount of water. Unexpectedly, in order to achieve reasonable activity (Table 9), the amount of water added to the organic-phase is found to be greater than the void volume of the support (60–70 µl). This suggests a relatively small partition coefficient of water between the CPG support and the ethyl acetate. A maximum water loading of 2.8–3.1 wt % (g H$_2$O/g AcOEt×100; i.e. ~275 μl water in 10 ml of ethyl acetate) was accomplished by using a water-saturated organic phase. The initial turnover frequencies as a function of water content are listed in Table 9 (reaction conditions: substrate/ruthenium~30, [substrate]= 4.6–4.8×10$^{-3}$M, pressure=1350–1400psig, T=25° C., stirring speed=350rpm). Water is introduced to the "dried" SAP catalyst from the ethyl acetate (10 ml) and the water content controlled by adding variable amounts of water, e.g., 0, 40, 125, 145, 160, 195, 215 and 270 μl. The maximum activity, as determined by the initial turnover frequency, is observed at the highest water content (~3 wt % water in ethyl acetate) with an initial turnover frequency of 18.2hr$^{-1}$. Table 9, Entry 8. The enantioselectivity of the SAP catalyst is also dependent on the water content and shows a similar trend to that observed in the activity; the observed range is 28.7% to 70.0% (R). Table 8, Entries 1 & 5. Thus, the water content affects the activity and enantioselectivity of the SAP catalyst.

The present findings are quite different from that which has been observed in the hydroformylation of 1-octene by a SAP-rhodium-TPPTS catalyst (Arhancet, et al. *J. Catal* (1990) 121:327). In the hydroformylation of 1-octene, catalyst activity was much more sensitive to the water content of the SAP catalyst with a bell-shaped curve that describes the activity dependence on water content. Maximum activity was observed at ~8 wt % (gH$_2$O/g SAPC×100) water content and complete loss of activity was observed at ~50 wt %. Arhancet, et al. *J. Catal* (1990) 121:327.

Two factors appear to be responsible for the difference in behavior towards the water content of these two SAP catalysts. First, the [Ru(benzene)(BINAP-4SO$_3$Na)]$^{2+}$ complex is stable even in neat water while HRh(CO)(TPPTS)$_3$ is not stable at high syn gas pressure. At high water loading, the HRh(CO)(TPPTS)$_3$ complex decomposes, resulting in a drop in activity. Second, the decrease in the interfacial surface area of the SAP material with increasing water loading also contributes to the rapid decline in the activity of the more hydrophilic SAP-Rh-TPPTS catalyst. Because of the small partition coefficient of water between the CPG support and the ethyl acetate, the actual amount of water being loaded onto the SAP-Ru-BINAP-4SO$_3$Na catalyst is far below the amount added by the vapor-phase impregnation into the much more hydrophilic SAP-Rh-TPPTS catalyst.

In view of the water content of ethyl acetate in the present SAP system, leaching of the catalytic species into the organic phase may be more likely. Filtration of the reaction mixture to remove the solid catalyst after the hydrogenation reaction yields a colorless solution of product in ethyl acetate. All filtrates were found not to contain any ruthenium at a detection limit of 1 ppm. Table 8, Entries 2, 4–5 & 15, Table 9, Entries 3–8. In addition, in some of the experiments, filtrates were tested indirectly for the presence of ruthenium by attempting the catalytic hydrogenation of methylenesuccinic acid using the filtrate alone as catalyst. In no case was catalytic activity observed in the filtered solutions. For example, filtered solutions gave no conversion of methylenesuccinic acid at room temperature after one day of contact under a pressure of 30 psig of hydrogen. The inactivity of these filtered solutions together with the elemental analyses suggest that no soluble ruthenium species have leached out into the organic phase.

It is reasonable to suggest that the ruthenium complex becomes increasingly mobile as water loading increases. This is evidenced from the data in Table 9 which shows that the hydrated SAP catalyst is at least 2000 times more active than the "dried" SAP catalyst. With a higher degree of mobility, the SAP catalyst can approach the same enantioselectivity as its counterpart in the two-phase system. Because of the much larger interfacial surface area between the catalyst containing aqueous-phase and the substrate containing organic-phase, the SAP system is found to be at least 50 times more active than the two-phase system. In the best cases, turn over frequencies obtained using hydrated SAP catalyst are only seven times slower than homogeneous catalyst in neat methanol under the same conditions. We have observed a similar drop (6.7 times) in initial turnover frequency in the homogeneous hydrogenation of methyl-2-acetamidoacrylate by [Rh(BINAP4SO$_3$Na) (H$_2$O)$_2$]$^+$ in neat water (Wan, et al. *J.C.S., Chem. Commun.* (1993) 1262), where both the substrate and the catalyst are mixed together in one single phase. We attribute the drop in turnover frequency of the rhodium system to the fact that hydrogen solubility is four to five times higher in alcoholic solvents. This factor is significant since the oxidative addition of hydrogen to the rhodium catalyst is rate determining.

The effect of added base on the SAP system was also examined. The results are listed in Table 8. The addition of either aqueous sodium hydroxide or triethylamine was found to have little effect on the enantioselectivity (Table 8, Entries 13, 15–16), although it does appear to promote the activity to some extent. In the presence of sodium hydroxide, the enantioselectivity was found to be rather pressure-insensitive in the pressure range of 500–1,400 psig. Table 8, Entries 17–19. The enantiomeric excesses were almost constant for the hydrated SAP catalyst in the pressure range of 500–1,400 psig. Table 8, Entries 2 & 3. Similar to the case of the homogeneous analogue, higher enantiomeric excesses (77%) are achieved with a lower reaction temperature of 8° C., but only at the expense of activity (T.O.F.=0.43hr$^{-1}$). The possibility of catalyst decomposition during the synthesis of SAP material is ruled out by the fact that a hydrogenation of 2-(6'-methoxy-2'-naphthyl) acrylic acid with an 86% e.e. was accomplished using a redissolved catalyst solution from a used SAP catalyst in methanol. Thus, the ruthenium complex is still stable in the SAP configuration. It is therefore apparent that the performance of the hydrated SAP catalyst is bounded by the intrinsic enantioselectivity limit of the ruthenium sulfonated BINAP catalyst in water. Additionally, it is clear that the SAP solid support plays no important role in enantioselectivity.

A series of reactions were carried out to test the possibility of recycling the SAP catalyst. The used SAP catalyst was removed from the hydrogenation mixture by simple filtration. It was then washed several times with fresh ethyl acetate, followed by the addition of fresh substrate and solvent. Similar e.e. values (65–70t%) were found throughout the recycling of the SAP catalyst Table 8, Entries 2, 4–5; 6–8 & 9–11.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for conducting an asymmetric reaction to a prochiral unsaturated bond contained within a compound comprising the step of contacting said compound with a supported highly-polar liquid-phase catalyst comprising an organometallic compound which comprises a metal and an enantiomerically pure chiral sulfonated 2,2'-bis (diphenylphosphino)-1,1'-binaphthyl, wherein each phenyl group of the sulfonated binaphthyl is monosulfonated, and wherein the degree to which the sulfonated binaphthyl is sulfonated is selected from the group consisting of tetrasulfonated, pentasulfonated, and hexasulfonated.

2. The method of claim 1 wherein the highly-polar liquid-phase comprises ethylene glycol.

3. A method according to claim 1 wherein the metal is selected from the group consisting of rhodium, ruthenium, iridium, vanadium, lead, platinum, tin, nickel and palladium.

4. A method according to claim 1 wherein the catalyst further comprises a counterion selected from the group consisting of $Na^+$, $K^+$, $Cs^+$ and $Ca^{2+}$.

5. The method of claim 1 wherein the enantiomerically pure chiral sulfonated 2,2'-bis(diphenylphosphino)-1,1'-binaphthyl is sulfonated (R)2,2'-bis(diphenylphosphino)-1,1'-binaphthyl.

6. A method for conducting an asymmetric reaction to a prochiral unsaturated bond contained within a compound comprising the step of contacting said compound with a supported highly-polar liquid-phase catalyst comprising an organometallic compound which comprises a metal and a chiral sulfonated 2,2'-bis(diphenylphosphino)-1,1'-binaphthyl, wherein each phenyl group of the sulfonated binaphthyl is monosulfonated, wherein the degree to which the sulfonated binaphthyl is sulfonated is selected from the group consisting of tetrasulfonated, pentasulfonated, and hexasulfonated, and wherein the highly-polar liquid-phase comprises ethylene glycol.

7. A method according to claim 6 wherein the asymmetric reaction is selected from the group consisting of hydrogenation, hydroboration, hydrosilylation, hydride reduction, hydroformylation, alkylation, allylic alkylation, arylation, alkenylation, epoxidation, hydrocyanation, cyclization and disilylation.

8. A method according to claim 6 wherein the metal is selected from the group consisting of rhodium, ruthenium, iridium, vanadium, lead, platinum, tin, nickel and palladium.

9. A method according to claim 6 wherein the catalyst further comprises a counterion selected from the group consisting of $Na^+$, $K^+$, $Cs^+$ and $Ca^{2+}$.

10. A method for conducting an asymmetric reaction to a prochiral unsaturated bond contained within a compound comprising the step of contacting said compound with a supported aqueous phase catalyst comprising an organometallic compound which comprises a metal and a chiral sulfonated 2,2'-bis(diphenylphosphino)-1,1'-binaphthyl, wherein each phenyl group of the sulfonated binaphthyl is monosulfonated, and wherein the decree to which the sulfonated binaphthyl is sulfonated is selected from the group consisting of tetrasulfonated, pentasulfonated, and hexasulfonated.

11. A method according to claim 10 wherein the asymmetric reaction is selected from the group consisting of hydrogenation, hydroboration, hydrosilylation, hydride reduction, hydroformylation, alkylation, allylic alkylation, arylation, alkenylation, epoxidation, hydrocyanation, cyclization and disilylation.

12. A method according to claim 10 wherein the metal is selected from the group consisting of rhodium, ruthenium, iridium, vanadium, lead, platinum, tin, nickel and palladium.

13. A method according to claim 10 wherein the the catalyst further comprises a counterion selected from the group consisting of $Na^+$, $K^+$, $Cs^+$ and $Ca^{2+}$.

14. A method of asymmetrically hydrogenating a 2-arylacrylic acid comprising the step of treating the 2-arylacrylic acid with hydrogen in the presence of a supported highly-polar liquid-phase catalyst comprising a metal and a chiral sulfonated 2,2'-bis(diphenylphosphino)-1,1'-binaphthyl, wherein each phenyl group of the sulfonated binaphthyl is monosulfonated, and wherein the decree to which the sulfonated binaphthyl is sulfonated is selected from the group consisting of tetrasulfonated, pentasulfonated, and hexasulfonated.

15. A method according to claim 14 wherein the metal is selected from the group consisting of rhodium, ruthenium, iridium, vanadium, lead, platinum, tin, nickel and palladium.

16. A method according to claim 14 wherein the 2-arylacrylic acid is dehydronaproxen.

17. A method according to claim 14 wherein the the catalyst further comprises a counterion selected from the group consisting of $Na^+$, $K^+$, $Cs^+$ and $Ca^{2+}$.

* * * * *